US012694985B2

(12) United States Patent　　　　(10) Patent No.: US 12,694,985 B2
Kano et al.　　　　　　　　　　　　　(45) Date of Patent: Jul. 28, 2026

(54) CLINICAL DECISION SUPPORT DEVICE, CLINICAL DECISION SUPPORT METHOD, AND STORAGE MEDIUM

(71) Applicant: Canon Kabushiki Kaisha, Tokyo (JP)

(72) Inventors: Yusuke Kano, Nasushiobara (JP); Minoru Nakatsugawa, Yokohama (JP); Anri Yamazaki, Nasushiobara (JP); Kosuke Arita, Nasushiobara (JP)

(73) Assignee: Canon Kabushiki Kaisha, Tokyo (JP)

( * ) Notice: Subject to any disclaimer, the term of this patent is extended or adjusted under 35 U.S.C. 154(b) by 101 days.

(21) Appl. No.: 18/364,577

(22) Filed: Aug. 3, 2023

(65) Prior Publication Data

US 2024/0047066 A1　　Feb. 8, 2024

(30) Foreign Application Priority Data

Aug. 8, 2022　(JP) ................................. 2022-126295

(51) Int. Cl.
　　*G16H 50/20*　　　(2018.01)
　　*G16H 10/20*　　　(2018.01)
(52) U.S. Cl.
　　CPC ............. *G16H 50/20* (2018.01); *G16H 10/20* (2018.01)
(58) Field of Classification Search
　　None
　　See application file for complete search history.

(56) References Cited

U.S. PATENT DOCUMENTS

| 10,482,183 | B1 * | 11/2019 | Vargas | ................... | G06F 40/30 |
| 2013/0304660 | A1 * | 11/2013 | Bohmfalk | .............. | G06Q 40/08 |
| | | | | | 705/322 |
| 2023/0121812 | A1 * | 4/2023 | Yin | ...................... | G06V 10/774 |
| | | | | | 706/15 |
| 2023/0162532 | A1 * | 5/2023 | Ratha | ..................... | G06V 40/23 |
| | | | | | 382/103 |

FOREIGN PATENT DOCUMENTS

| JP | 2021-12437 A | 2/2021 | |
| WO | WO-2014174404 A1 * | 10/2014 | ........... G06F 17/289 |

OTHER PUBLICATIONS

Fang, Q., Nguyen, D., & Oberski, D. L. (2022). Evaluating the construct validity of text embeddings with application to survey questions. EPJ Data Science, 11(1), 39. doi:http://dx.doi.org/10. 1140/epjds/s13688-022-00353-7 (Year: 2022).*

* cited by examiner

*Primary Examiner* — Robert A Sorey
(74) *Attorney, Agent, or Firm* — Oblon, McClelland, Maier & Neustadt, L.L.P.

(57)　　　　　ABSTRACT

A clinical decision support device of an embodiment includes processing circuitry. The processing circuitry acquires at least one of attribute information of a patient and first parameters regarding a first preference category for the patient. The processing circuitry estimates second parameters of the patient with respect to a second preference category on the basis of at least one of the attribute information and the first preference category. The processing circuitry determines preferable selections of the patient with respect to a predetermined preference category on the basis of the second parameters. The processing circuitry displays the preferable selections and the second parameters in association with each other.

12 Claims, 7 Drawing Sheets

FIG. 6

MEANINGS OF BOTH
QUESTION AND ANSWER ARE
INCLUDED IN SENTENCE

| Patient | Preference |
|---------|------------|
| A | Sentence01 |
| A | Sentence02 |
| B | Sentence03 |
| ... | |

Embedding

Question Vector

Embedding

Patient Vector

PRODUCT ⊗

Rating

CLINICAL DECISION SUPPORT DEVICE, CLINICAL DECISION SUPPORT METHOD, AND STORAGE MEDIUM

CROSS-REFERENCE TO RELATED APPLICATION

The present application claims priority based on Japanese Patent Application No. 2022-126295 filed Aug. 8, 2022, the content of which is incorporated herein by reference.

FIELD OF THE INVENTION

Background of the Invention

Embodiments of the present invention relate to a clinical decision support device, a clinical decision support method, and a storage medium.

Description of Related Art

In recent years, shared decision making, in which patients and medical staff discuss treatment goals, treatment preferences and values and work together to find the best treatment, has become important. Therefore, conventionally, there is a technique of identifying characteristics of a patient on the basis of preferences and preferable selections of the patient and recommending a treatment matching the characteristics. However, it takes a lot of time and effort to draw out the preferences of a patient through conversation. In addition, although the preferences of a patient include not only those with a high degree of importance but also those with a low degree of importance, it is impossible to know the preferences in advance, and thus there are cases in which preferences emphasized by a patient cannot be efficiently acquired.

BRIEF DESCRIPTION OF THE DRAWINGS

FIG. 6 is a diagram for describing an example of processing of the estimation function in a third pattern.

DETAILED DESCRIPTION OF THE INVENTION

Hereinafter, a clinical decision support device, a clinical decision support method, and a storage medium of embodiments will be described with reference to the drawings.

A clinical decision support device of an embodiment includes processing circuitry. The processing circuitry acquires at least one of attribute information of a patient and first parameters regarding a first preference category for the patient. The processing circuitry estimates second parameters of the patient regarding a second preference category on the basis of the at least one of the attribute information and the first preference category. The processing circuitry determines preferable selections of the patient regarding a predetermined preference category on the basis of the second parameters. The processing circuitry displays the preferable selections and the second parameters in association with each other.

Figure 1:
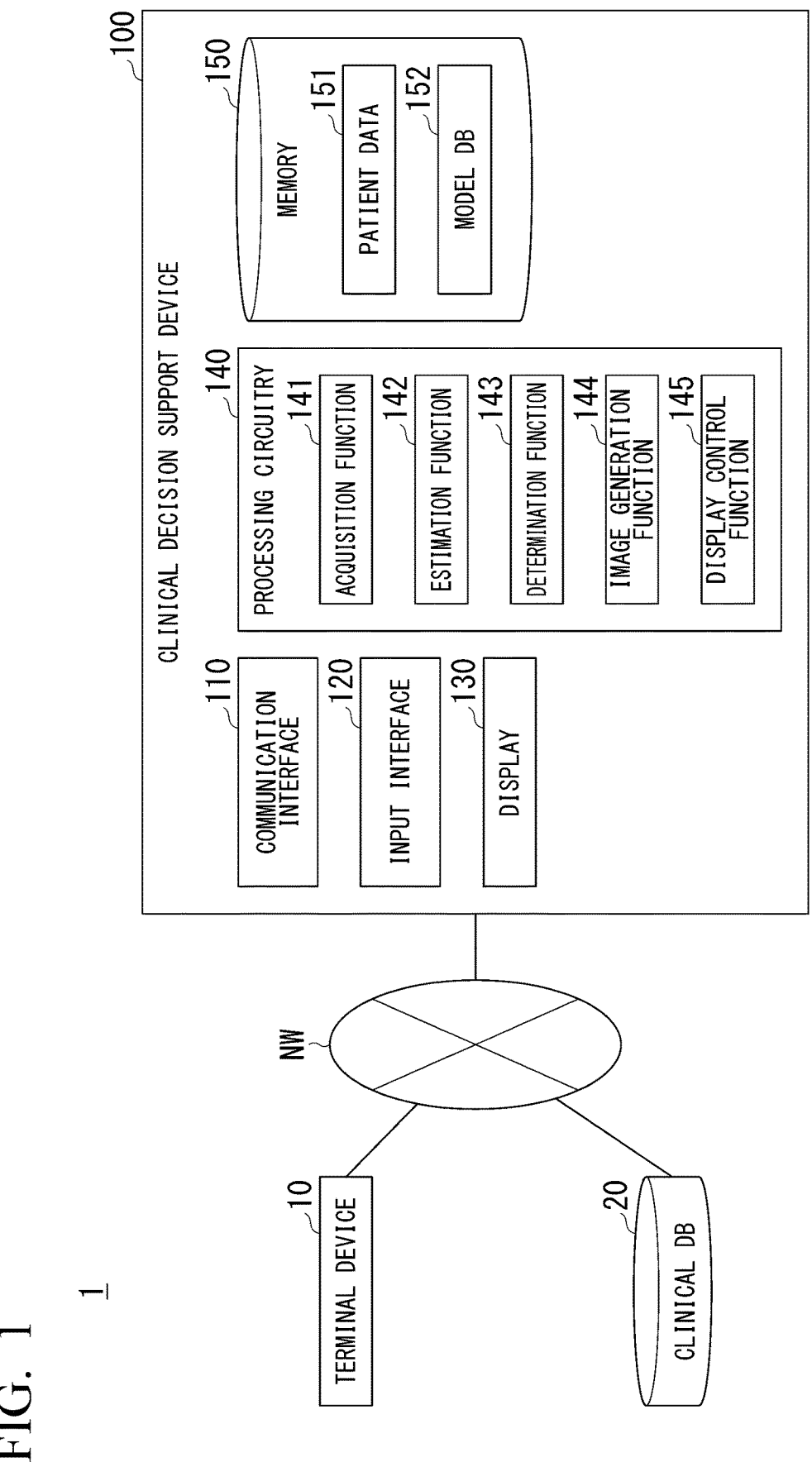
FIG. 1 is a diagram showing an example of a configuration of a clinical decision support system including a clinical decision support device according to an embodiment.

FIG. 1 is a diagram showing an example configuration of a clinical decision support system 1 including a clinical decision support device according to an embodiment. The clinical decision support system 1 includes, for example, a terminal device 10, a clinical DB 20, and a clinical decision support device 100. The terminal device 10, the clinical DB 20, and the clinical decision support device 100 are connected via a network NW, for example, such that they can communicate. At least one of the terminal device 10 and the clinical DB 20 may be provided in the clinical decision support system 1.

The network NW represents general information communication networks using telecommunication technology. The network NW includes, for example, a wireless/wired local area network (LAN), a wide area network (WAN), an Internet network, a telephone communication network, an optical fiber communication network, a cable communication network, a satellite communication network, or the like.

The terminal device 10 may be, for example, a terminal device for a patient (an example of a subject) to input attribute information, first parameters regarding the first preference category, or the like or a terminal device for a medical staff member to input attribute information of a patient and first parameters. Attribute information includes, for example, objective information that is taken into account when a medical staff member makes a clinical decision regarding a target patient. For example, attribute information may include information on clinical aspects such as disease types and subtypes and opinions on examinations, and information on social aspects such as family composition and economic conditions. In addition, attribute information may include the name of a patient, identification information (for example, ID) for identifying the patient, opinions regarding preferences of the patient, and the like. The first preference category is preference information regarding a predetermined treatment, such as life expectancy, appearance after treatment, cost, a treatment period, and the like. The first parameters include an index value (degree of importance) indicating how much a patient emphasizes the first preference category. The first parameters are subjective information on psychological aspects regarding medical treatment of the target patient and include an index value indicating a degree of satisfaction considered when the patient compares a plurality of clinical determinations. The first parameters may be synonymous with utility in economics. In the present embodiment, the aforementioned index value is quantified as a degree of importance. Although the first preference category is defined in advance by the clinical decision support system 1 in the following description, the present invention is not limited thereto and the first preference category may be provided in a format such as natural language. Further, quantified preferences may be normalized for an individual to clarify superiority or inferiority. It is possible to curb variations in input values between individuals through normalization. Medical staff include, for example, doctors and nurses (clinical decision makers) who determine the content of medical treatments for patients.

The terminal device 10 receives inputs regarding attribute information and the first parameters from a patient and a medical staff member and transmits the received attribute information and first parameters to the clinical decision support device 100 via the network NW. In addition to the attribute information and the first parameters, the terminal device 10 may receive patient diagnosis data (for example, diagnosis history and biometric data) and the like and transmit the received information to the clinical decision support device 100 via the network NW. Further, the terminal device 10 may transmit various types of received information to the clinical DB 20 via the network NW.

The terminal device 10 is a device including functions of executing the above-described processing and is, for example, a smartphone, a tablet terminal, a general-purpose personal computer (PC), or a server device. Further, the terminal device 10 may be a terminal device included in a clinical decision support (CDS) system.

The clinical DB 20 is a database in which patient attribute information, first parameters, clinical data, and the like are stored. The clinical DB 20 stores, for example, patient attribute information, first parameters, clinical data, and the like acquired by the terminal device 10 or other external devices in the database. The clinical DB 20 transmits the patient attribute information, first parameters, clinical data, and the like to the clinical decision support device 100 via the network NW. Further, the clinical DB 20 may store data transmitted from the clinical decision support device 100. The clinical DB 20 may be, for example, a general-purpose server, a cloud server, or the like.

The clinical decision support device 100 acquires various types of information on a patient transmitted from the terminal device 10 or the clinical DB and presents support information regarding a medical treatment for the patient to a medical staff member on the basis of the acquired information. The clinical decision support device 100 displays processing results on a display thereof or transmits the processing results to the terminal device 10 via the network NW. The clinical decision support device 100 may be, for example, a smartphone, a tablet terminal, a general-purpose PC, a server device, or a cloud server.

Here, a functional configuration of the clinical decision support device 100 will be described. The clinical decision support device 100 includes, for example, a communication interface 110, an input interface 120, a display 130, processing circuitry 140, and a memory 150.

The communication interface 110 includes, for example, a communication interface such as a network interface controller (NIC). The communication interface 110 communicates with external devices such as the terminal device 10 and the clinical DB 20 via the network NW and outputs acquired information to the processing circuitry 140 and the like. In addition, the communication interface 110 is controlled by the processing circuitry 140 to transmit information to external devices such as the terminal device 10 and the clinical DB 20 connected via the network NW.

The input interface 120 receives various input operations from a user, converts the accepted input operations into electrical signals, and transmits the electrical signals to the processing circuitry 140. For example, when an input operation is performed by the user, the input interface 120 generates information in response to the input operation. The input interface 120 transmits the generated information in response to the input operation to the processing circuitry 140. The input interface 120 is realized by, for example, a mouse, a keyboard, a trackball, a switch, buttons, a joystick, a touch panel, or the like. Further, the input interface 120 may be realized by, for example, a user interface that receives voice input, such as a microphone. When the input interface 120 is a touch panel, the display 130 which will be described later may be formed integrally with the input interface 120.

The display 130 displays various types of information. For example, the display 130 displays an image generated by the processing circuitry 140, a graphical user interface (GUI) for receiving various input operations from the user, and the like. For example, the display 130 is a liquid crystal display (LCD), a cathode ray tube (CRT) display, an organic electroluminescence (EL) display, or the like.

The processing circuitry 140 includes, for example, an acquisition function 141, an estimation function 142, a determination function 143, an image generation function 144, and a display control function 145. The processing circuitry 140 realizes these functions by, for example, a hardware processor executing a program stored in a storage device (storage circuit).

The hardware processor means, for example, circuitry such as a central processing unit (CPU), a graphics processing unit (GPU), an application specific integrated circuit (ASIC), and a programmable logic device (for example, a simple programmable logic device (SPLD), a complex programmable logic device (CPLD), or a field programmable gate array (FPGA)).

Instead of storing the program in the storage device, the program may be configured to be directly embedded in the circuit of the hardware processor. In this case, the hardware processor realizes the functions by reading and executing the program embedded in the circuit. The aforementioned program may be stored in a storage device in advance or may be stored in a non-transitory storage medium such as a DVD or CD-ROM and installed in the storage device from the non-transitory storage medium when the non-transitory storage medium is set in a drive device (not shown) of the clinical decision support device 100.

The hardware processor is not limited to being configured as a single circuit and may be configured as a single hardware processor by combining multiple independent circuits to realize each function. Further, a plurality of components may be integrated into one hardware processor to realize each function.

The memory 150 is realized by, for example, a semiconductor memory device such as a random access memory (RAM) or a flash memory, a hard disk, an optical disc, or the like. Such a non-transitory storage medium may be realized by other storage devices such as a network attached storage (NAS) and an external storage server device connected via the network NW. Moreover, such a non-transitory storage medium may be realized by a storage device such as a read only memory (ROM) and a register. The memory 150 stores, for example, patient data 151, a model DB 152, programs, and other various types of information.

The acquisition function 141 acquires at least one of attribute information of a patient and first parameters regarding the first preference category for the patient, transmitted from the terminal device 10 or the clinical DB 20 via the communication interface 110. Further, the acquisition function 141 may acquire at least one of the attribute information of the patient and the first parameters through input from the input interface 120. Further, the acquisition function 141 may store the acquired patient information and the first parameters in the patient data 151. Furthermore, the acquisition function 141 may acquire clinical data and attributes (for example, occupation and employment history, and viewpoints emphasized in medical determination) about medical staff (doctors and nurses) who use the clinical decision support system 1 in addition to the attribute information and the first parameters regarding the target patient. By acquiring attribute information on the medical staff, the acquisition function 141 can provide support information for efficiently acquiring preferences emphasized by the patient for each medical staff member supporting depending on the attributes of the medical staff used (for example, doctors and nurses) for the same patient.

The estimation function 142 estimates second parameters of the patient regarding a second preference category on the basis of the at least one of the attribute information and the first parameters. The second parameters are, for example, parameters including a degree of importance and uncertainty of the patient regarding the second preference category. The second preference category may be the same as or different from the first preference category. For example, the estimation function 142 estimates degrees of importance and uncertainties of the patient with respect to unacquired preference categories that are not included in the first parameters on the basis of the attribute information and preference information of the patient. The estimation function 142 may estimate at least some (e.g., age) of attribute information that has not been acquired by the acquisition function 141 in addition to (or instead of) the content described above.

Figure 2:
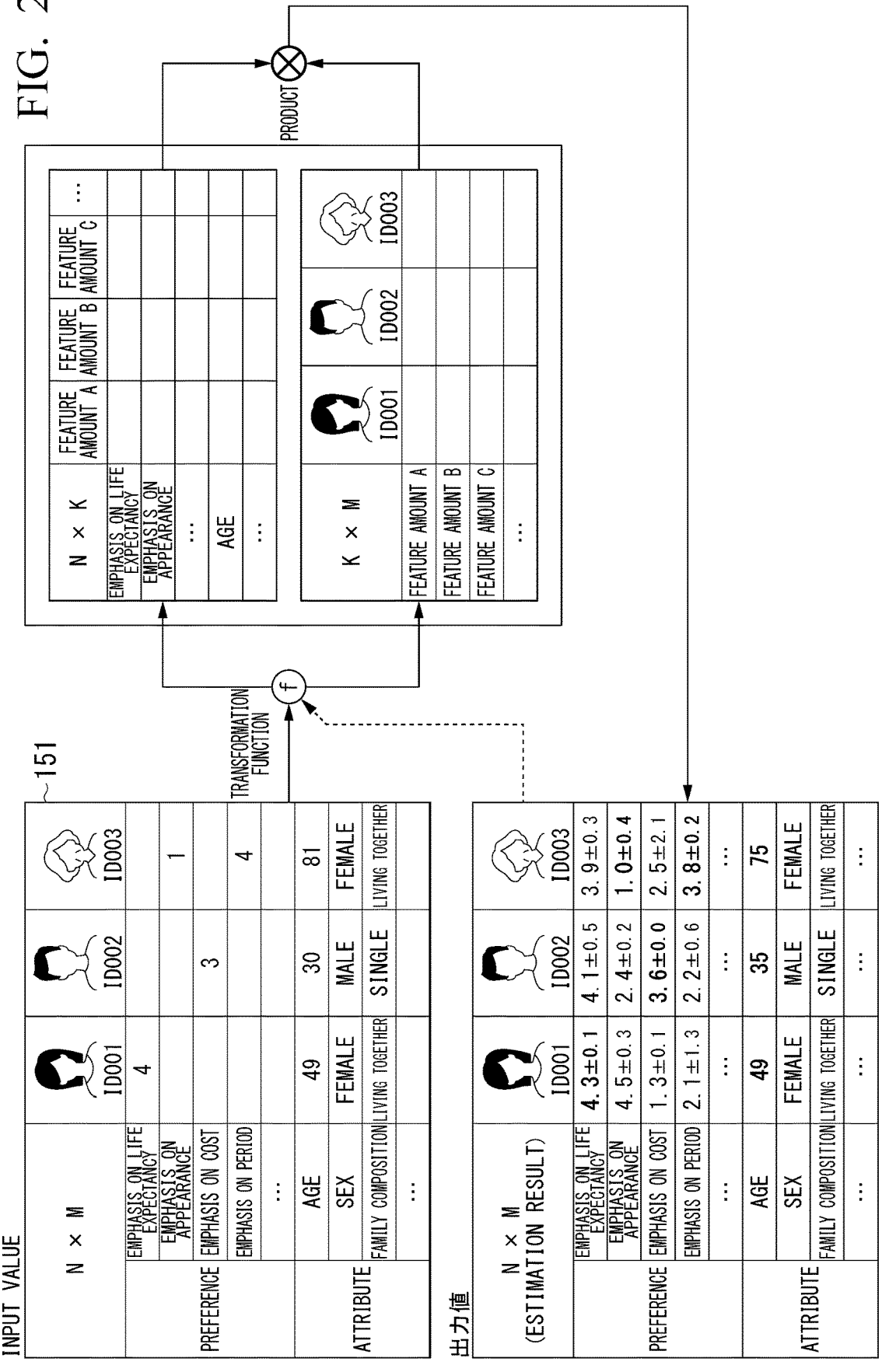
FIG. 2 is a diagram for describing an estimation function.

FIG. 2 is a diagram for describing the estimation function 142. The estimation function 142 estimates degrees of importance and the like for items (predetermined categories) that have not been input among a plurality of items (elements) included in first parameters including attribute information and preference information of a patient using an estimation model stored in the model DB 152 in the memory 150. In the example of FIG. 2, the attribute information includes, for example, age, sex, and family composition and the preference information includes, for example, degrees of importance such as emphasis on life expectancy, emphasis on appearance, emphasis on cost, and emphasis on period, but the present invention is not limited thereto.

Here, the estimation model is trained by, for example, preferences (or preferences and attributes) and matrix factorization for matrices represented by patients. For example, the estimation function 142 performs estimation through collaborative filtering using information on other patients who have similar preferences to a certain patient. The estimation function 142 represents an N×M matrix as the product of two matrices of N×K and K×M, for example, as shown in FIG. 2, on the assumption that a dimension of the first parameters (or first parameters+attribute information) that are input values is N, the number of patients used for training is M, and a dimension of feature amounts is K. A feature amount is, for example, an element such as a field (genre) regarding preferences or attributes and is arbitrarily extracted in machine learning or the like without relying on human intervention.

Then, the estimation function 142 outputs estimation results obtained by estimating each value in the N×M matrix on the basis of the result of the product as output values. In this case, as shown in FIG. 2, the estimation function 142 not only interpolates (matrix-interpolates) degrees of importance of preference categories that are not included in the input values, but also estimates degrees of importance of preference categories included in the input values by the estimation model.

In addition, the estimation function 142 learns a transformation function f of matrix factorization such that error (estimation error) between a degree of importance estimated for a preference category of the output values and a degree of importance of the same preference category present as an input value is minimized. For example, the estimation function 142 performs feedback control or the like on the estimation results on the basis of results of respective values of preference attribute information and feature amounts A, B, C, . . . , feature amounts A, B, and C, and patient information and learns the transformation function f such that the transformation function becomes values (having errors within a predetermined range) close to degrees of importance of preferences actually input as the first parameters, as shown in FIG. 2. Then, the estimation function 142 estimates final second parameters regarding the second preference category using the transformation function f that has become close values. In the example of FIG. 2, the type of second preference category is the same as the first preference category. In addition, the estimation function 142 outputs the N×M matrix as second parameters including an error range (for example, ±0.1 or the like) as estimation results. This error range is an example of an index value indicating uncertainty.

Incidentally, training of the estimation model is typically performed by matrix factorization using singular value decomposition, as described above, but the present invention is not limited thereto and a known method using a known neural network may be used, for example. In addition, the estimation function 142 may perform estimation considering uncertainty by combining Bayesian estimation. In matrix factorization, using a neural network is equivalent to using a Bayesian neural network. A Bayesian neural network is realized, for example, by using a dropout function (for example, a function of learning while randomly disabling some nodes on the network) in a neural network.

In addition, although the estimation function 142 can acquire degrees of importance for preference categories that are not included in the first parameters as estimation results (output values from the estimation model), the estimation results may be used with respect to values of preference categories that have been originally acquired as the input values, or the input values may be used as they are. When the degree of importance of the preference categories included in the input values are used as the second parameters, an index value indicating uncertainty may not be output because it is reliable information of the patient.

The estimation function 142 may perform the above-described estimation processing each time input values change or every predetermined period. It is possible to acquire more accurate second parameters by executing the estimation processing in response to change in the input values.

The determination function 143 determines preferable selections of a patient (information that is estimated to be "selected by the patient's preference") with respect to a predetermined preference category (including categories different from the second preference category) on the basis of the second parameters regarding the second preference category estimated by the estimation function 142. For example, the determination function 143 determines how much the patient emphasizes the predetermined preference category based on the determined preferable selections of the patient.

Further, the determination function 143 may also determine priorities regarding the preferable selections of the patient with respect to a plurality of predetermined preference categories on the basis of the second parameters. For example, the determination function 143 determines priorities on the basis of an upper bound on uncertainties of preferences estimated for each patient with respect to a plurality of predetermined preference categories. The upper bound is, for example, an upper limit value of a 95% confidence interval, or the like. That is, the determination function 143 determines that the upper bound is a large value and the priorities are high when uncertainty is high even if it is not necessarily large as the mode of an estimated distribution.

A priority determination method is not limited to an upper bound, and a priority may be determined, for example, using only the magnitude of uncertainty. In this case, the determination function 143 increases priorities regarding the preferable selections of the patient as uncertainty for the second preference category included in the second parameters increases. Further, the determination function 143 determines that there is little additional information obtained through conversations with the patient with respect to preferences with low uncertainty, and thus the priorities are interpreted as low.

The determination function 143 may also assign priorities to preferences originally included in the input values. For example, if the input values significantly differ from estimated values, the determination function 143 determines that preferences of the patient may have changed since acquisition and assigns a high priority. Accordingly, a priority can be determined more appropriately for each preference.

The image generation function 144 associates the preferable selections of the patient determined by the determination function 143 with the second parameters and generates an image to be displayed on the display 130 or the like.

The display control function 145 causes the image generated by the image generation function 144 to be displayed on the display 130 or to be transmitted to the terminal device 10, the clinical DB 20, or the like via the network NW. In addition, the display control function 145 may cause the image generation function 144 to generate an image or perform change of display content, and the like according to an instruction from the user. In addition, the display control function 145 may store processing results and the like in the memory 150 and cause information stored in the memory 150 to be displayed on the display 130 or to be transmitted to the terminal device 10, the clinical DB 20, or the like.

Figure 3:
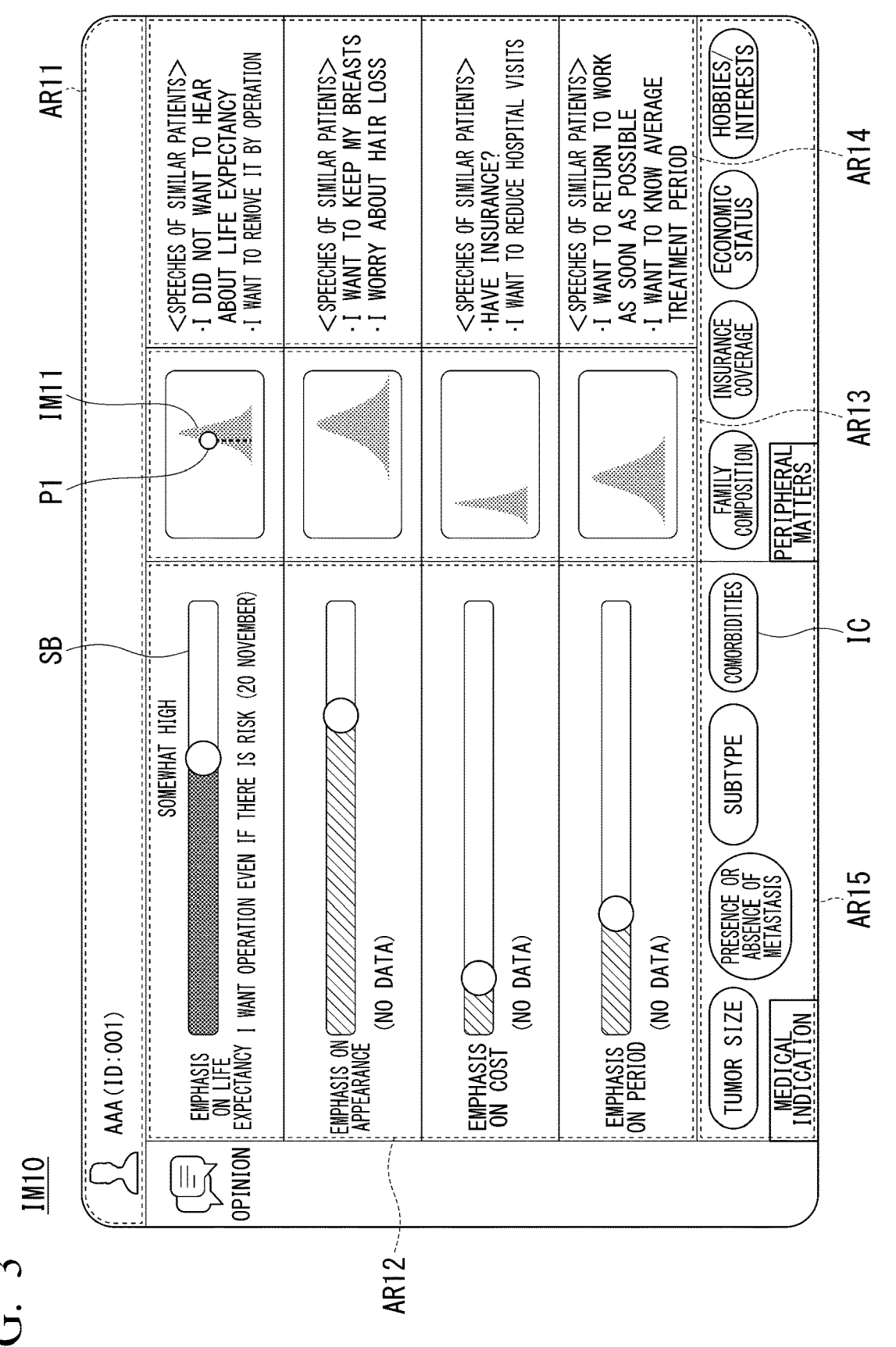
FIG. 3 is a diagram showing an example of an image generated by an image generation function.

FIG. 3 is a diagram showing an example of an image IM10 generated by the image generation function 144. The content, layout, colors, font, design, and other display modes displayed in image IM10, which will be described below, are not limited thereto. The image IM10 includes, for example, a patient information display area AR11, a preference information display area AR12, a distribution display area AR13, a similar patient display area AR14, and a related information display area AR15.

Attribute information of a patient, such as a patient identification ID, is displayed in the patient information display area AR11, for example. Information on the degree of importance for each of preference categories (emphasis on life expectancy, emphasis on appearance, emphasis on cost, and emphasis on period) of the patient is displayed in the preference information display area AR12. Preference categories determined by the determination function 143 may be displayed in descending order of priority in the preference information display area AR12. Further, the preference information display area AR12 is provided with a slide bar SB or the like for each preference. Upon receiving an operation on the slide bar SB by a user (medical staff member or patient), the display control function 145 changes a degree of importance of the preference category according to the operation of the slide bar SB.

A distribution image IM11 that indicates preferences of the target patient with respect to a predetermined preference category or uncertainty of prediction thereof is displayed in the distribution display area AR13, for example. Here, the position of the distribution image IM11 is set, for example, on the basis of the average value of degrees of importance for the same preference for each patient, and the horizontal width of the distribution image IM11 increases as uncertainty increases. By displaying the distribution image IM11 in this way, it is possible to easily visually recognize preferences with high uncertainty, and thus a medical staff member can obtain an opinion of the patient by asking the patient about the preferences, for example.

The display control function 145 displays a position corresponding to a slid value (degree of importance) on the distribution image IM11 as a point P1 in association with shifting of the slide bar SB in the preference information display area AR12 with respect to a predetermined preference category (in other words, in accordance with change in the degree of importance). Accordingly, it is possible to more accurately ascertain a position in the distribution representing the uncertainty of the patient, to which the degree of importance corresponding to the preference category corresponds.

In addition, the image generation function 144 acquires information on other patients (for example, similar patients) from the patient data 151 in association with shifting of the slide bar SB with respect to the predetermined preference category (in response to change in the degree of importance). Further, the image generation function 144 may also identify similar patients to the target patient on the basis of a degree of similarity to a preference estimation value estimated by the estimation function 142, and acquire information on the similar patients. Further, the similar patients may be patients whose attribute information, including sex and age, is more similar among a plurality of patients. Information on similar patients is opinions of other patients (speeches of patients) who have set the same preferences (degrees of importance) for the same preference category as a preference category for which the slide bar SB is being shifted and, for example, is free text answers. The display control function 145 causes the image generation function 144 to generate an image including the acquired similar patient information and displays the image in the similar patient display area AR14. Accordingly, by shifting the slide bar SB, opinions of similar patients at the position thereof can be acquired, and thus it is possible to easily select the degree of importance corresponding to an opinion that suits user's preferences. In addition, the user can curb setting errors between individuals by setting a degree of importance while referring to opinions of others.

For information on similar patients, different patients may be set for each preference category. In addition, since the position corresponding to the slid value (degree of importance) on the distribution image IM11 described above is the point P, and the information on the similar patients is used as an auxiliary function at the time of answering degrees of importance of preferences of the patient, the display control function 145 dynamically switches and displays the point P and the information on the similar patients even before preference values are input or confirmed.

In addition, when the estimation function 142 executes estimation processing and display content is updated each time the first parameters for the target patient are acquired, the display control function 145 may display the changed content before and after update.

The related information display area AR15 displays icons IC for displaying and inputting medical indication information and information on peripheral matters of the patient.

The medical indication information is, for example, information based on medical examination results of the patient and is information on a tumor size, presence or absence of metastasis, a subtype indicating sub-attributes of the patient, and comorbidities. In addition, the information on the peripheral matters of the patient includes information for displaying informative indication information, information regarding family composition, insurance coverage, economic status, hobbies and interests, and the like. The number of icons IC displayed in the related information display area AR15 is not limited thereto. Further, the image IM10 may not include the related information display area AR15.

Modified Examples

Figure 4:
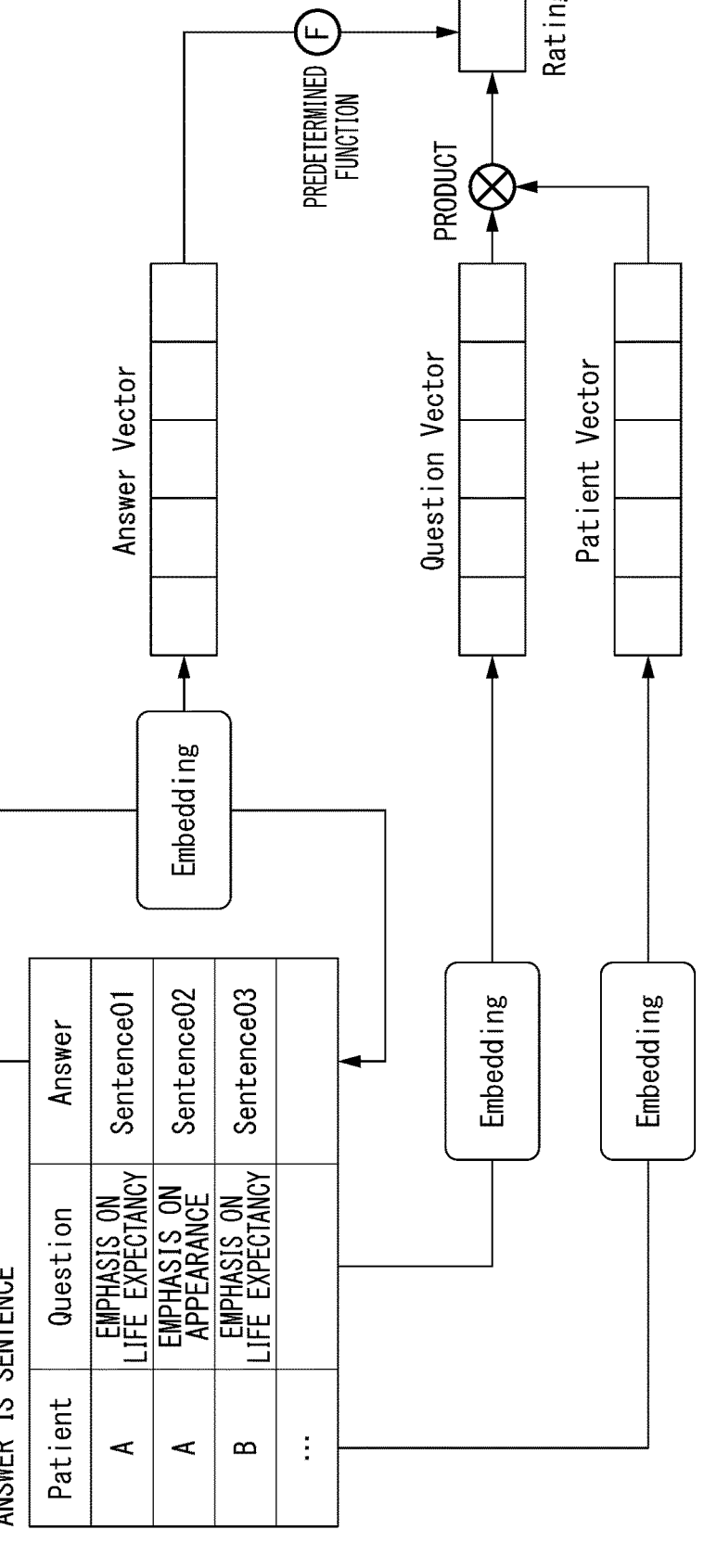
FIG. 4 is a diagram for describing an example of processing of the estimation function in a first pattern.

Although items regarding preferences (for example, emphasis on life expectancy, emphasis on appearance, emphasis on cost, and emphasis on period) in the first parameters are defined in advance by the clinical decision support system 1 and treated as categorical data in the above-described embodiment, instead of (or in addition to) defining the items, questions or answers regarding preferences may be provided in at least one sentence (natural language). Patterns of provided data include, for example, a first pattern in which an answer is a sentence, a second pattern in which a question is a sentence, and a third pattern in which both a question and an answer are included in a sentence. An example of processing of the estimation function 142 in each pattern will be described below.
<First Pattern>
FIG. 4 is a diagram for describing an example of processing of the estimation function 142 in the first pattern. In the first pattern, the estimation function 142 estimates values in a certain vector by mapping a certain feature amount to another dimension using an embedding technique in natural language processing, for example, for each of a patient's attribute (Patient), a question (Question), and an answer (Answer).

Figure 5:
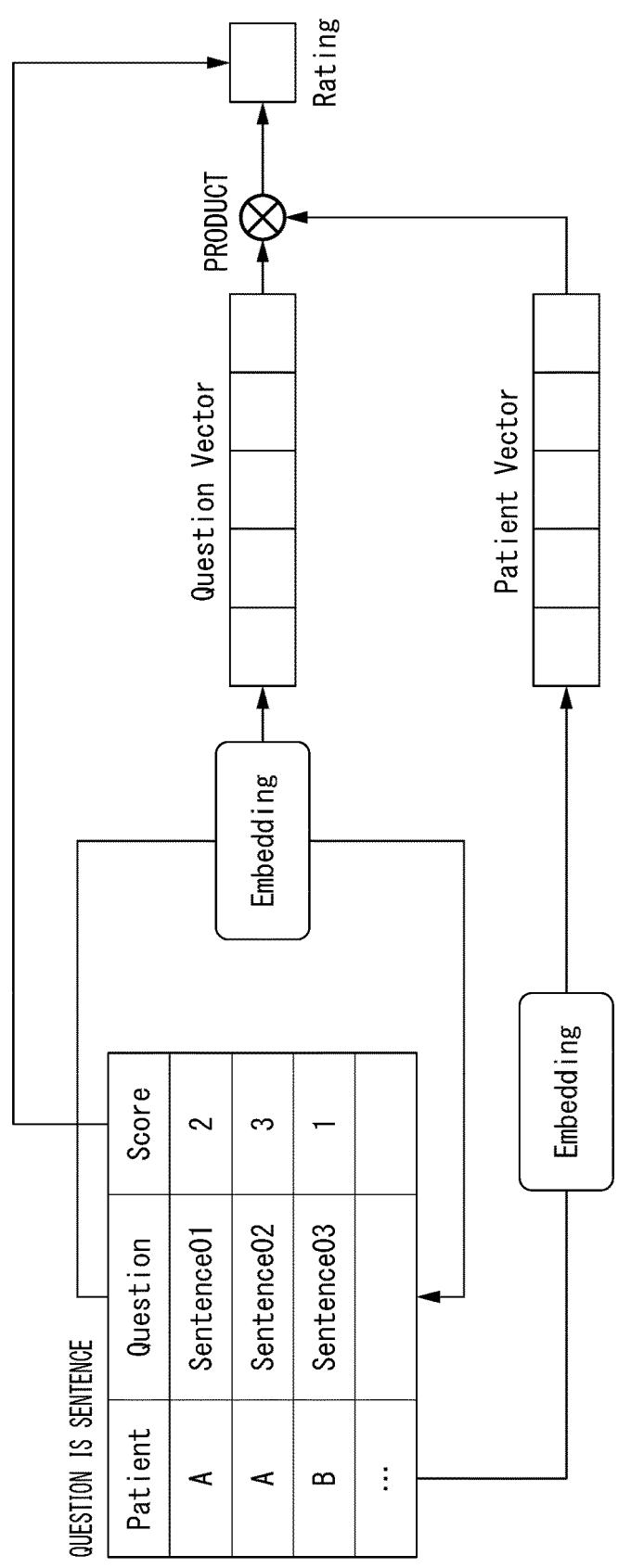
FIG. 5 is a diagram for describing an example of processing of the estimation function in a second pattern.

In the first pattern, the estimation function 142 performs language analysis processing on sentences included in answers and acquires series information (for example, feature amounts such as constituent elements such as words, character strings, and sentence strings) obtained as analysis results. Next, the estimation function 142 generates vector information (Answer Vector) regarding the answers while performing embedding on the obtained series information (feature amount) through a technique such as Sequence-to-Sequence (Seq2Seq) that is a model that returns another series (feature amounts), or Doc2Vec that converts a sentence having an arbitrary length into a fixed-length vector. Further, in the first pattern, the estimation function 142 generates vector information (Patient Vector and Question Vector) using the embedding technique for patient's attributes (Patient) and questions (Question) and learns to rate output results on the basis of the product of the generated vectors and values obtained from the vector information regarding the answers through a predetermined function. The above-described embedding may be different from embedding for natural languages. For example, in the first pattern, an "answer" is a sentence in a natural language, but an "attribute" and a "question" of a patient are not in a natural language. Therefore, for "attribute" and "question," embedding processing is performed on numerical values or category data (type and classification), and this processing includes, for example, one-hot encoding and the like. The above-described processing is the same for items that are not expressed in sentences in second and third patterns, which will be described later. In the first pattern, an estimated score is estimated for each preference.
<Second Pattern>
FIG. 5 is a diagram for describing an example of processing of the estimation function 142 in the second pattern. In the second pattern, a question is a sentence pattern, language analysis processing is performed on sentences included in questions, embedding is performed using a technique such as Seq2Seq or Doc2Vec, and vector information (Question Vector) with respect to the questions is generated. In addition, the estimation function 142 learns to rate output results by comparing the product of the vector information (Question Vector) with respect to the questions and vector information (Patient Vector) obtained using the embedding technique for patient's attributes (Patient) with scores (Score) acquired as answers from patients. In the second pattern, estimated scores are estimated for question sentences answered by other patients. According to the second pattern, for example, it is possible to predict the content of an answer at the time of asking the same question as a question sentence answered by another patient on the basis of rating results.
<Third Pattern>
FIG. 6 is a diagram for describing an example of processing of the estimation function 142 in the third pattern. In the third pattern, the patient data 151 is associated with patient's attributes (Patient) and sentences (Preference), and the sentences include the content of both questions and answers. As an example of a sentence (Preference), "I want to minimize changes in appearance such as hair loss such that people around me will not notice that I am undergoing cancer treatment" or the like is assumed. In the third pattern, the estimation function 142 acquires vector information with respect to questions using, for example, language analysis processing of sentences and the embedding technique, and learns to rate output results by comparing the product of the vector information and vector information (Patient Vector) acquired from the patient's attributes using the embedding technique with results of the Question Vector. In the third pattern, sentences answered by other patients and estimated scores are estimated.

Figure 7:
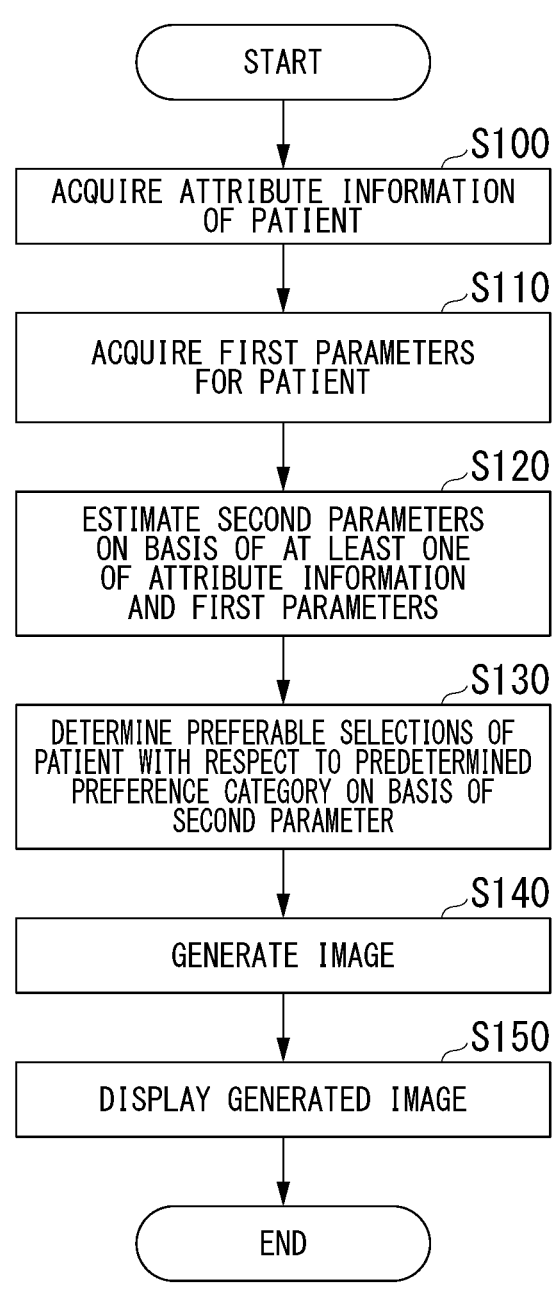
FIG. 7 is a flowchart showing a series of processes executed by processing circuitry.

Each of the first to third patterns described above may be combined with some or all of the other patterns.
[Processing Flow]
A processing flow of the processing circuitry 140 in the embodiment will be described below. FIG. 7 is a flowchart showing a series of processing executed by the processing circuitry 140. In the example of FIG. 7, the acquisition function 141 acquires attribute information of a patient (step S100) and acquires first parameters regarding the first preference category for the patient (step S110).

Next, the estimation function 142 estimates second parameters regarding the second preference category on the basis of at least one of the attribute information and the first parameters (step S120). Next, the determination function 143 determines preferable selections of the patient with respect to a predetermined preference category on the basis of the second parameters (step S130). Next, the image generation function 144 generates an image including the determined preferable selection information (step S140). Next, the display control function 145 causes the display 130 to display the image generated by the image generation function 144 (step S150). In the processing of step S150, the generated image may be transmitted to an external device (the terminal device 10 or the clinical DB 20) via the network NW. Accordingly, processing of this flowchart ends.

In the above-described embodiment, the acquisition function 141 is an example of an "acquisition unit", the estimation function 142 is an example of an "estimation unit", the determination function 143 is an example of a "determination unit", the image generation function 144 is an example of an "image generation unit," and the display control function 145 is an example of a "display control unit."

According to at least one embodiment described above, the clinical decision support device of the embodiment can provide support information for efficiently acquiring preferences emphasized by a patient by including an acquisition unit that acquires at least one of attribute information of the patient and first parameters regarding the first preference category for the patient, an estimation unit that estimates second parameters of the patient with respect to the second preference category on the basis of at least one of the attribute information and the first preference category, a determination unit that determines preferable selections of the patient with respect to a predetermined preference category on the basis of the second parameters, and a display control unit that displays the preferable selections and the second parameters in association with each other.

Specifically, according to embodiments, it is possible to determine the order (priority) of content of conversations with the patient more appropriately by providing support information that allows medical staff to efficiently draw out the preferences emphasized by the patient. Further, according to embodiments, medical staff can focus their time and efforts on obtaining preferences with a high degree of importance. In addition, according to embodiments, medical staff can more accurately ascertain the degree of understanding of patient' preferences regarding medical treatment.

The above-described embodiments can be represented as follows.

A clinical decision support device including processing circuitry, wherein the processing circuitry is configured to:

acquire at least one of attribute information of a patient and first parameters regarding a first preference category for the patient;

estimate second parameters of the patient with respect to a second preference category on the basis of at least one of the attribute information and the first preference category;

determine preferable selections of the patient with respect to a predetermined preference category on the basis of the second parameters; and display the preferable selections and the second parameters in association with each other.

Although several embodiments have been described, these embodiments are presented as examples and are not intended to limit the scope of the invention. These embodiments can be implemented in various other forms, and various omissions, substitutions, and modifications can be made without departing from the spirit of the invention. These embodiments and modifications thereof are included in the scope and spirit of the invention, as well as the scope of the invention described in the claims and equivalents thereof.

What is claimed is:

1. A clinical decision support device comprising processing circuitry configured to:

acquire at least one of attribute information of a patient and first parameters regarding a first preference category for the patient by input from an external device capable of communicating via a network, or an input interface;

estimate second parameters of the patient with respect to a second preference category by inputting at least one of the attribute information and the first preference category to an estimation model;

determine preferable selections of the patient with respect to a predetermined preference category on the basis of the second parameters;

generate information that associates the preferable selections and the second parameters with each other and an image for inputting a change to the second parameters;

display the information and the image on a display;

generate vector information using an embedding technique to generate a patient attribute vector, a question vector, and an answer vector;

form a product vector of the question vector and the answer vector; and use the patient attribute vector and the product vector to produce a rating value, wherein the processing circuitry receives a change to the second parameters inputted through the input interface, changes the second parameters in response to the received change, and displays opinions of other patients for the same preference category on the display in association with the change to the second parameters, wherein the estimation model is trained by Matrix Factorization over a matrix represented by preferences and attributes of the patient and one or more patient feature amounts, wherein the processing circuitry learns a transformation function for the matrix factorization so as to minimize an error between the second parameters with respect to the second preference category and the first parameters of the same preference category included in at least one of the attribute information and the first preference category, and estimates the second parameters of the patient with respect to the second preference category using the learned transformation function, and wherein, when the first parameters include a sentence in a natural language, the processing circuitry estimates the second parameters of the patient by performing language analysis on a patient attribute, question and answer.

2. The clinical decision support device according to claim 1, wherein the processing circuitry determines preferable selections of the patient with respect to a plurality of predetermined preference categories.

3. The clinical decision support device according to claim 2, wherein the processing circuitry further determines priorities for the preferable selections of the patient with respect to the plurality of predetermined preference categories.

4. The clinical decision support device according to claim 3, wherein the processing circuitry increases the priorities for the preferable selections of the patient as uncertainties for the second preference category included in the second parameters increase.

5. The clinical decision support device according to claim 1, wherein the second parameters are parameters including degrees of importance and uncertainties of the patient regarding the second preference category.

6. The clinical decision support device according to claim 1, wherein the processing circuitry displays a distribution image showing uncertainty regarding the predetermined preference category.

7. The clinical decision support device according to claim 1, wherein, when the first parameters include a sentence in a natural language, the processing circuitry estimates the second parameters of the patient using an embedding technique for mapping a feature amount of the sentence to a vector of another dimension.

8. The clinical decision support device according to claim 1, wherein the processing circuitry changes and displays opinions of other patients on the same preference category in response to change in degrees of importance for the predetermined preference category.

9. The clinical decision support device according to claim 1, wherein the processing circuitry generates and displays a distribution indicating preferences of a target patient with respect to the second preference category, generates a user-operable slide bar for the second preference category, and generates a point on the distribution movable in association with moving the slide bar to indicate a position in the distribution representing uncertainty of the patient.

10. A clinical decision support method, using a computer, comprising:

acquiring at least one of attribute information of a patient and first parameters regarding a first preference category for the patient by input from an external device capable of communicating via a network, or an input interface;

estimating second parameters of the patient with respect to a second preference category by inputting at least one of the attribute information and the first preference category to an estimation model;

determining preferable selections of the patient with respect to a predetermined preference category on the basis of the second parameters;

generating information that associates the preferable selections and the second parameters with each other and an image for inputting a change to the second parameters;

displaying the information and the image on a display;

receiving a change to the second parameters inputted through the input interface;

changing the second parameters in response to the received change;

displaying opinions of other patients for the same preference category on the display in association with the change to the second parameters;

generating vector information using an embedding technique to generate a patient attribute vector, a question vector, and an answer vector;

forming a product vector of the question vector and the answer vector; and using the patient attribute vector and the product vector to produce a rating value, wherein the estimation model is trained by Matrix Factorization over a matrix represented by preferences and attributes of the patient and one or more patient feature amounts, wherein the method further comprises learning a transformation function for the matrix factorization so as to minimize an error between the second parameters with respect to the second preference category and the first parameters of the same preference category included in at least one of the attribute information and the first preference category, and estimating the second parameters of the patient with respect to the second preference category using the learned transformation function, and wherein, when the first parameters include a sentence in a natural language, the estimating the second parameters of the patient comprises performing language analysis on a patient attribute, question and answer.

11. A non-transitory computer-readable recording medium storing a program causing a computer to:

acquire at least one of attribute information of a patient and first parameters regarding a first preference category for the patient by input from an external device capable of communicating via a network, or an input interface;

estimate second parameters of the patient with respect to a second preference category by inputting at least one of the attribute information and the first preference category to an estimation model;

determine preferable selections of the patient with respect to a predetermined preference category on the basis of the second parameters;

generating information that associates the preferable selections and the second parameters with each other and an image for inputting a change to the second parameters;

display the information and the image on a display;

receive a change to the second parameters inputted through the input interface;

change the second parameters in response to the received change;

display opinions of other patients for the same preference category on the display in association with the change to the second parameters;

generate vector information using an embedding technique to generate a patient attribute vector, a question vector, and an answer vector;

form a product vector of the question vector and the answer vector; and use the patient attribute vector and the product vector to produce a rating value, wherein the estimation model is trained by Matrix Factorization over a matrix represented by preferences and attributes of the patient and one or more patient feature amounts, wherein the program causes to the computer to learn a transformation function for the matrix factorization so as to minimize an error between the second parameters with respect to the second preference category and the first parameters of the same preference category included in at least one of the attribute information and the first preference category, and estimate the second parameters of the patient with respect to the second preference category using the learned transformation function, and wherein, when the first parameters include a sentence in a natural language, the program causes the computer to estimate the second parameters of the patient by performing language analysis on a patient attribute, question and answer.

12. A clinical decision support device comprising processing circuitry configured to:

acquire at least one of attribute information of a patient and first parameters regarding a first preference category for the patient by input from an external device capable of communicating via a network, or an input interface;

estimate second parameters of the patient with respect to a second preference category by inputting at least one of the attribute information and the first preference category to an estimation model;

determine preferable selections of the patient with respect to a predetermined preference category on the basis of the second parameters;

generate information that associates the preferable selections and the second parameters with each other and an image for inputting a change to the second parameters; and display the information and the image on a display, wherein the processing circuitry receives a change to the second parameters inputted through the input interface, changes the second parameters in response to the received change, and displays opinions of other patients for the same preference category on the display in association with the change to the second parameters, wherein the estimation model is trained by Matrix Factorization over a matrix represented by preferences and attributes of the patient and one or more patient feature amounts, and wherein the processing circuitry learns a transformation function for the matrix factorization so as to minimize an error between the second parameters with respect to the second preference category and the first parameters of the same preference category included in at least one of the attribute information and the first preference category, and estimates the second parameters of the patient with respect to the second preference category using the learned transformation function.

*   *   *   *   *